United States Patent
Ni et al.

(10) Patent No.: US 11,543,292 B1
(45) Date of Patent: Jan. 3, 2023

(54) LOW-FREQUENCY NOISE CANCELLATION IN OPTICAL MEASUREMENTS

(71) Applicant: Analog Devices International Unlimited Company, Limerick (IE)

(72) Inventors: Jinhua Ni, Shanghai (CN); Hui Shen, Shanghai (CN)

(73) Assignee: Analog Devices International Unlimited Company, Limerick (IE)

( * ) Notice: Subject to any disclaimer, the term of this patent is extended or adjusted under 35 U.S.C. 154(b) by 0 days.

(21) Appl. No.: 17/412,542

(22) Filed: Aug. 26, 2021

Related U.S. Application Data

(63) Continuation of application No. PCT/CN2021/109624, filed on Jul. 30, 2021.

(51) Int. Cl.
*G01J 1/44* (2006.01)
*A61B 5/1455* (2006.01)
*G01N 33/49* (2006.01)

(52) U.S. Cl.
CPC ............. *G01J 1/44* (2013.01); *A61B 5/14552* (2013.01); *G01J 2001/444* (2013.01); *G01N 33/4925* (2013.01)

(58) Field of Classification Search
CPC ... G01J 1/44; G01J 2001/444; A61B 5/14552; G01N 33/4925
See application file for complete search history.

(56) References Cited

U.S. PATENT DOCUMENTS

| | | |
|---|---|---|
| 9,203,350 B2 | 12/2015 | Dempsey et al. |
| 9,900,018 B1 | 2/2018 | Chen et al. |
| 2005/0045807 A1 | 3/2005 | Sakaguchi |
| 2009/0163784 A1* | 6/2009 | Sarpeshkar ............. H03F 1/342 330/98 |
| 2013/0021018 A1 | 1/2013 | Venkataraman et al. |
| 2015/0257663 A1 | 9/2015 | Deliwala |
| 2018/0156660 A1* | 6/2018 | Turgeon ................... G09G 5/10 |
| 2020/0037901 A1* | 2/2020 | Trattler .............. A61B 5/02416 |
| 2020/0178865 A1* | 6/2020 | Trattler ..................... G01J 1/44 |
| 2020/0375483 A1* | 12/2020 | Bremer ................ A61B 5/7225 |
| 2021/0123801 A1 | 4/2021 | Liu |
| 2021/0270965 A1 | 9/2021 | Liu et al. |

FOREIGN PATENT DOCUMENTS

DE  102017127963 A1  5/2019

OTHER PUBLICATIONS

"Low-Power Photoplethysmogram Acquisition Integrated Circuit with Robust Light Interference Compensation," by Jongpal Kim et al .; Sensors, vol. 16, Published Dec. 31, 2015 (Year: 2015).*

* cited by examiner

*Primary Examiner* — Thanh Luu
*Assistant Examiner* — Monica T Taba
(74) *Attorney, Agent, or Firm* — Akona IP PC

(57) ABSTRACT

Low-frequency Noise Cancellation Method for Optical Measurement Systems. The present disclosure provides a low frequency noise cancellation method for optical measurement system, An optical measurement system has a transmitter to drive an LED and a receiver connected to a photodiode. The LED driver will generate a pulse signal to drive the LED and act as the radiation source for the optical measurement. Consequently, the receiver will convert the received photo-diode current to a voltage signal. The signal will then be digitized by an ADC for further processing. A current DAC circuit IDAC is added at the front of the receiver and has the same timing control with the LED driver to cancel the DC portion of the received current.

20 Claims, 9 Drawing Sheets

LOW-FREQUENCY NOISE CANCELLATION IN OPTICAL MEASUREMENTS

CROSS-REFERENCE TO RELATED APPLICATIONS

This application is a continuation of and claims the benefit of priority under 35 U.S.C. § 120 and 35 U.S.C. § 363 to International Application No. PCT/CN2021/109624 entitled, "LOW-FREQUENCY NOISE CANCELLATION METHOD FOR OPTICAL MEASUREMENTS" filed on Jul. 30, 2021, which is hereby incorporates by reference in its entirety.

FIELD OF THE DISCLOSURE

Embodiments of the invention are directed, in general, to electronic systems and, more specifically, to a low noise, low power front end for a pulsed input system and methods using same.

BACKGROUND

Flicker noise is a type of electronic noise with a 1/f power spectral density. It is therefore often referred to as 1/f noise or pink noise, though these terms have wider definitions. It occurs in almost all electronic devices and can show up with a variety of other effects, such as impurities in a conductive channel, generation and recombination noise in a transistor due to base current, and so on.

1/f noise in current or voltage is usually related to a direct current, as resistance fluctuations are transformed to voltage or current fluctuations by Ohm's law. There is also a 1/f component in resistors with no direct current through them, likely due to temperature fluctuations modulating the resistance. This effect is not present in manganin, as it has negligible temperature coefficient of resistance.

In electronic devices, it shows up as a low-frequency phenomenon, as the higher frequencies are overshadowed by white noise from other sources. In oscillators, however, the low-frequency noise can be mixed up to frequencies dose to the carrier, which results in oscillator phase noise.

Flicker noise is often characterized by the corner frequency $f_c$ between the region dominated by the low-frequency flicker noise and the higher-frequency "flat-band" noise. MOSFETs have a higher $f_c$ (can be in the GHz range) than JFETs or bipolar transistors, which is usually below 2 kHz for the latter.

It typically has a Gaussian distribution and is time-reversible. It is generates by a linear mechanism in resistors and FETs, but a non-linear mechanism in BJTs and diodes.

The flicker-noise voltage power in MOSFET is often modeled as:

$$\frac{K}{C_{ox} \cdot WLf}$$

where, K is the process-dependent constant, $C_{ox}$ is the oxide capacitance in MOSFET devices, W and L are channel width and length respectively. This is an empirical model and generally thought to be an oversimplification.

Oximeters are photoelectric devices which measure the oxygen saturation of blood. Historically, these devices were first used in clinical laboratories on samples of blood taken from patients. In recent years, non-invasive oximeters have been developed and are now widely used in intensive care units to monitor critically ill patients and in operating rooms to monitor patients under anesthesia. Early non-invasive devices relied on dialization of the vascular bed in, for example, the patient's ear lobe to obtain a pool of arterial blood upon which to perform the saturation measurement.

More recently, non-invasive devices known as "pulse oximeters" have been developed which rely on the patient's pulse to produce a changing amount of arterial blood in, for example, the patient's finger or other selected extremity. Pulse oximeters for home use are small, lightweight monitors that painlessly attach to a fingertip to monitor the amount of oxygen carried in the body. An oxygen level of greater than 95% is generally considered to be a normal oxygen level. An oxygen level of 92% or less (at sea level) suggests a low blood oxygen.

Pulse oximetry is a noninvasive method for monitoring a person's oxygen saturation ($SO_2$). Though its reading of $SpO_2$ (peripheral oxygen saturation) is not always identical to the more desirable reading of SaO2 (arterial oxygen saturation) from arterial blood gas analysis, the two are correlated well enough that the safe, convenient, noninvasive, inexpensive pulse oximetry method is valuable for measuring oxygen saturation in clinical use.

Pulse oximeters measure oxygen saturation by (1) passing light of two more selected wavelengths, e.g., a "red" wavelength and an "IR" wavelength, through the patient's extremity, (2) detecting the time-varying light intensity transmitted through the extremity for each of the wavelengths, and (3) calculating oxygen saturation values for the patient's blood using the: Lambert-Beers transmittance law and the detected transmitted light intensities at the selected wavelengths.

Less commonly, reflectance pulse oximetry is used as an alternative to transmissive pulse oximetry described above. This method does not require a thin section of the person's body and is therefore well suited to a universal application such as the feet, forehead, and chest, but it also has some limitations. Vasodilation and pooling of venous blood in the head due to compromised venous return to the heart can cause a combination of arterial and venous pulsations in the forehead region and lead to spurious SpO2 results. Such conditions occur while undergoing anesthesia with endotracheal intubation and mechanical ventilation or in patients in the Trendelenburg position.

For people with COPD, asthma, Congestive Heart Failure (CHF) and other conditions, puke oximetry is a technology used to measure the oxygen level in your blood and your heart rate. Using a clip to a patient's fingertip, a finger pulse oximeter is equipped with technology to detect changes in your blood oxygen level.

In its most common (transmissive) application mode, a sensor device is placed on a thin part of the patient's body, usually a fingertip or earlobe, or in the case of an infant, across a foot. The device passes two wavelengths of light through the body part to a photodetector. It measures the changing absorbance at each of the wavelengths, allowing it to determine the absorbances due to the pulsing arterial blood alone, excluding venous blood, skin, bone, muscle, fat, and (in most cases) nail polish.

A plethysmograph (PPG) detector is a device for measuring biological events within body tissue. Using a plethysmograph (PPG) detector, and other devices for detecting biological events, operate by measuring changes in transmission or diffuse reflectance from the body tissue or subject under active illumination.

The radiation used for measuring plethysmograph (PPG) signals can span wavelengths from blue to infrared. In classic applications, light emitting diodes (LEDs) of two colors—often 660 nm and 940 nm—are used for measuring blood oxygen saturation. These devices are in large volume production and are readily available. In yet another application, a simple single-color LED—say at 940 nm—may be used to measure heart rate by measuring the periodic variation in a return signal. In some cases, a green LED is used to pick up variation in absorption caused by blood flow on the wrist.

Plethysmograph (PPG) signals are generated by measuring the changes in the transmission or diffuse reflectance of body tissue under active illumination by LED of a particular wavelength. The beating of the heart changes both the mechanical dimensions of the arteries and also blood volume in those arteries. These effects lead to variation in the received light intensity. A typical plethysmograph (PPG) signal makes a signal estimate required to measure parameters such as blood oxygen.

There is (developing interest to measure plethysmograph (PPG) signals continuously by incorporating plethysmograph (PPG) sensors/systems in devices that can be attached to a subject, for example, wrist band, watch, in-the-ear buds, etc. In such applications, these devices have to function with very low power and every photon emitted from the LED is precious as it is a drain on a battery. Furthermore, space constraints force the use of small photodiodes to collect diffuse light coming from the tissue. As a result, the signal is small and any reduction in noise of the system can be immediately applied to conserve battery power and increase the time to recharge or replace batteries.

Thus, much attention has been paid to reduce the noise of the receiver systems and noise in the LED drive circuits. Many noise reduction techniques for LED drivers and receivers require extra power. To make matters worse, many visible light LEDs themselves exhibit fairly large "1/f" noise in the generates light. This noise is a result of both 1/f noise in the LED driver as well as the physical mechanisms in the LED, such as the thermal fluctuations and the generation-recombination noise.

Since a heart beats at a relatively low frequency in the range of 0.5-5 Hz (30 to 300 beats per minute), this low frequency noise essentially limits the ability to measure the plethysmograph (PPG) signal. This becomes even more crucial for blood oxygen saturation (SpO2) systems where accurate determinations of both AC and DC components of the plethysmograph (PPG) signal must be made.

A survey of all commercially available PPG systems have $f_D$<0.01. Accordingly, the inventors perceive a need in the art for PPG system that permits reduction of noise in plethysmograph (PPG) signals captured by such systems. Additionally, there is a need for other vital sign monitors, such as, ECG, Biopotential, etc. to be incorporated into wearable devices.

Biopotential measurement is can be used in modern medical procedures. For example, biopotentials can be used for electrocardiogram (ECG), electroencephalogram (EEG), electromyography (EMG), etc.

ECG lead systems are used to obtain biopotential signals containing information indicative of the electrical activity associated with the heart and pulmonary system. To obtain biopotential signals, EGG electrodes are applied to the skin of a patient in various locations and coupled to an ECG device, e.g., an "ECG monitor" or "ECG telemetry." Placement of the electrodes is dependent on the information sought by the clinician.

The placement of the ECG electrodes on the patient has been established by medical protocols. The most common protocols require the placement of the electrodes in a three-lead, a five-lead, or a twelve-lead configuration. A three-lead configuration requires the placement of three electrodes; one electrode adjacent each clavicle bone (RA, LA) on the upper chest and a third electrode adjacent the patient's lower left abdomen (LL). A five-lead configuration requires the placement of the three electrodes in the three-lead configuration with the addition of a fourth electrode adjacent the sternum (Va) and a fifth electrode on the patient's lower right abdomen (RL). A twelve-lead configuration requires the placement of ten electrodes on the patient's body.

Four electrodes, which represent the patient's limbs, include the left arm electrode (LA lead), the right arm electrode (RA lead), the left leg electrode (LL lead), and the right leg electrode (RL lead), Six chest electrodes (V1-V6 leads) are placed on the patient's chest at various locations near the heart. Three standard limb leads are constructed from measurements between the right arm and left arm (Lead I), the right arm and the left leg (Lead II) and the left arm to left leg (Lead III). Other conventional lead configurations include a 14 leads system that incorporated additional leads located on a back surface.

An ECG lead set typically includes an array of three, five, or twelve cads as determined by the intended clinical protocol. Each individual lead wire includes, at a patient end thereof (e.g., distal end), an ECG cad wire connector configured to operably couple the lead wire to an electrode pad affixed to the body of a patient. At the opposite (e.g., proximal) end, the individual lead wires are gathered into a common coupler that is configured to operably couple the array of lead wires to an ECG device.

Leads sets are typically provided with a generous length of lead wire sufficient to reach from the patient to the ECG device. In some instances, however, the lead wire may fall short, in which case a lead wire extension cable having appropriate distal and proximal couplers may be employed. In some instances, the cad wire coupler of an ECG lead set and/or ECG lead extension may be incompatible with an available ECG device, in which case an ECG adapter may be employed that facilitates operable coupling of the otherwise-incompatible physical and/or electrical characteristics of the disparate couplers.

There is a demonstrated need in the art for a wearable device with the capacity to monitor a plurality of vital signs. The inventors of the present disclosure have recognized that an impediment to implementation is noise, and more specifically, background. As such, the inventors contemplate the cancellation of signals generated by ambient light in a dynamic environment.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

Low-frequency Noise Cancellation Method for Optical Measurement Systems. The present disclosure provides a low frequency noise cancellation method for optical measurement system. An optical measurement system has a transmitter to drive an LED and a receiver connected to a photodiode. The LED driver will generate a pulse signal to drive the LED and act as the radiation source for the optical measurement. Consequently, the receiver will convert the received photo-diode current to a voltage signal. The signal will then be digitized by an ADC for further processing. A current DAC circuit IDAC is added at the front of the receiver and has the same timing control with the LED driver to cancel the DC portion of the received current.

According to one aspect of the present disclosure, an apparatus and/or method for canceling low frequency noise comprises producing a signal waveform, receiving the waveform at a driver, producing light in response to the received signal waveform, illuminating an object with the light, receiving the light at a photodetector, compensating for the produced signal waveform with a current to voltage compensator, receiving the compensated signal at an optical receiver having an input and output, and sampling the output of the optical receiver with an analog to digital converter (ADC).

According to anyone of the preceding or proceeding aspects of the present disclosure, an apparatus and/or method for canceling low frequency noise, wherein one or more of ADC, driver, and current to voltage compensator share a reference voltage.

According to anyone of the preceding or proceeding aspects of the present disclosure, an apparatus and/or method for canceling low frequency noise, wherein the reference voltage is controlled by a timing circuit or oscillator.

According to anyone of the preceding or proceeding aspects of the present disclosure, an apparatus and/or method for canceling low frequency noise, wherein the ADC, driver, and current to voltage compensator are timed to the same produced waveform.

According to anyone of the preceding or proceeding aspects of the present disclosure, an apparatus and/or method for canceling low frequency noise, wherein the current to voltage compensator is an IDAC.

According to anyone of the preceding or proceeding aspects of the present disclosure, an apparatus and/or method for canceling low frequency noise, wherein the optical receiver is an op-amp.

According to anyone of the preceding or proceeding aspects of the present disclosure, an apparatus and/or method for canceling low frequency noise, wherein the light is produced by a light emitting diode (LED).

According to anyone of the preceding or proceeding aspects of the present disclosure, an apparatus and/or method for canceling low frequency noise, wherein the photodetector is a photodiode.

According to anyone of the preceding or proceeding aspects of the present disclosure, an apparatus and/or method for canceling low frequency noise, wherein the compensation includes subtracting the reference signal from the received photodetector signal.

According to anyone of the preceding or proceeding aspects of the present disclosure, an apparatus and/or method for canceling low frequency noise, wherein the signal waveform is a pulse train.

According to another aspect of the present disclosure, an apparatus and/or method for canceling low frequency noise comprises a driver configured to power a light source, a reference voltage generator for producing a voltage, Vref. a current source, a receiver in electrical communication with the current source, and an analog to digital converter (ADC) configured to sample the output of the receiver, wherein at least two of driver, current source, and ADC share Vref.

According to anyone of the preceding or proceeding aspects of the present disclosure, an apparatus and/or method for canceling low frequency noise further comprises a light sensor, the light sensor in electrical communication with the receiver and current source.

According to anyone of the preceding or proceeding aspects of the present disclosure, an apparatus and/or method for canceling low frequency noise further comprises a timing module, the timing module is in electrical communication with the reference voltage generator.

According to anyone of the preceding or proceeding aspects of the present disclosure, an apparatus and/or method for canceling low frequency noise, wherein the timing module is a dock circuit.

According to anyone of the preceding or proceeding aspects of the present disclosure, an apparatus and/or method for canceling low frequency noise, wherein the timing module comprises an oscillator.

According to anyone of the preceding or proceeding aspects of the present disclosure, an apparatus and/or method for canceling low frequency noise, wherein the driver, current source, and ADC share Vref.

According to anyone of the preceding or proceeding aspects of the present disclosure, an apparatus and/or method for canceling low frequency noise, wherein Vref is controlled by the timing module, at least in part.

According to anyone of the preceding or proceeding aspects of the present disclosure, an apparatus and/or method for canceling low frequency noise, wherein Vref is a pulse train.

According to anyone of the preceding or proceeding aspects of the present disclosure, an apparatus and/or method for canceling low frequency noise, wherein the current source is an IDAC and configured to maintain a current range received by the receiver.

According to another aspect of the present disclosure, an apparatus and/or method for canceling low frequency noise comprises a means for producing a signal waveform, a means for receiving the waveform at a driver, a means for producing light in response to the received signal waveform, a means for illuminating an object with the light, means for receiving the light at a photodetector, a means for compensating for the produces signal waveform with a current to voltage compensator, a means for receiving the compensated signal at an optical receiver having an input and output, and a means for sampling the output of the optical receiver with an analog to digital converter (ADC).

The drawings show exemplary optical front ends and configurations. Variations of these circuits, for example, changing the positions of, adding, or removing certain elements from the circuits are not beyond the scope of the present invention. The illustrated circuits, configurations, and complementary devices are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which.

DETAILED DESCRIPTION

Figure 1:
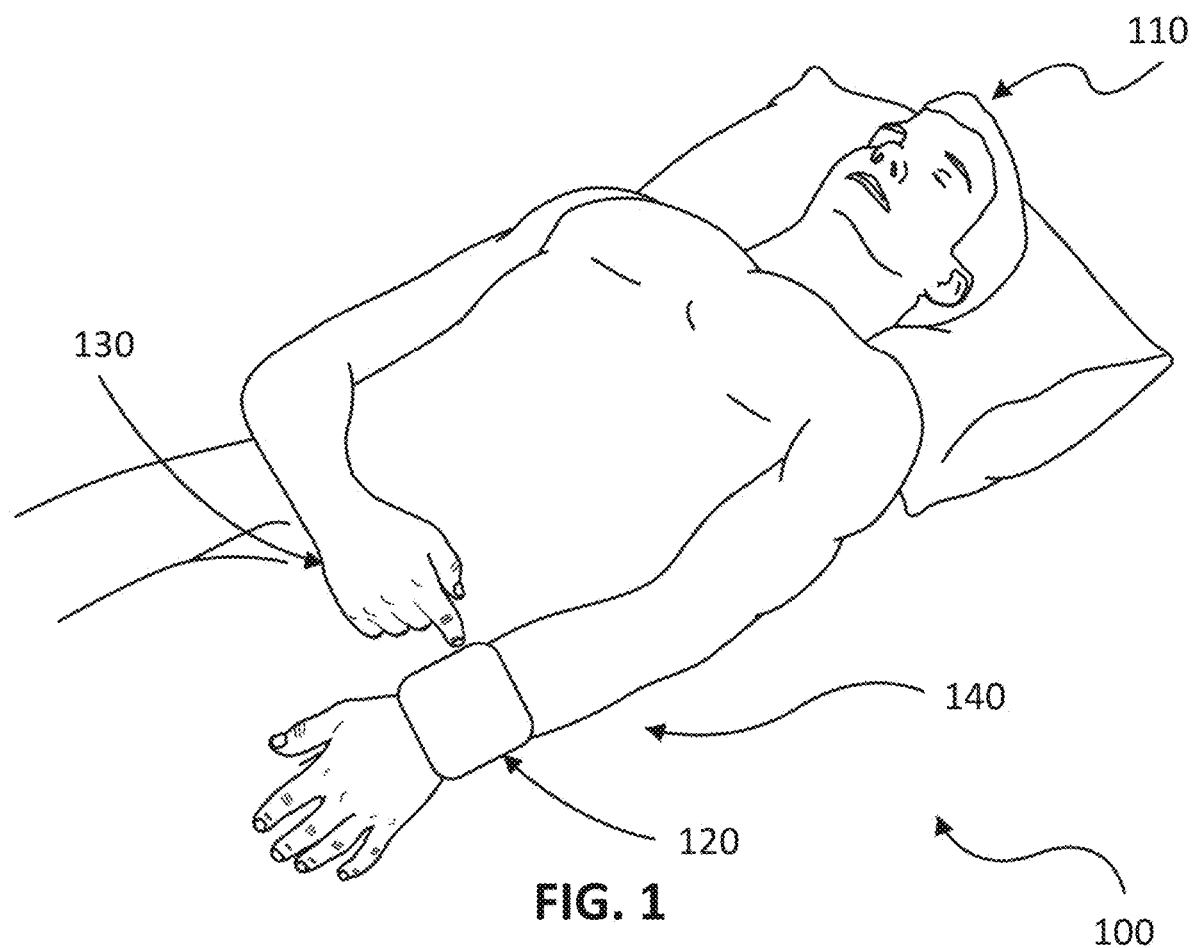
FIG. 1 depicts an exemplary wearable vital sign monitor (VSM), in accordance with some embodiments of the disclosure provided herein.

Low-frequency Noise Cancellation Method for Optical Measurement Systems. The present disclosure provides a low frequency noise cancellation method for optical measurement system. An optical measurement system has a transmitter to drive an LED and a receiver connected to a photodiode. The LED driver will generate a puke signal to drive the LED and act as the radiation source for the optical measurement. Consequently, the receiver will convert the received photo-diode current to a voltage signal. The signal will then be digitized by an ADC for further processing. A current DAC circuit IDAC is added at the front of the receiver and has the same timing control with the LED driver to cancel the DC portion of the receives current.

The present invention relates to plethysmography ("PPG") detectors and other devices that detect biological events and, in particular, improving signal-to-noise ratios ("SNR") per unit of expended power that is uses to gather PPG signals. Broadly, optical measurements comprise a transmitter to drive an LED a receiver connected to a photodiode. The LED driver will generate a pulse signal to drive the LED and act as the radiation source for the optical measurement. The receiver converts the received photo-diode current to voltage signal which is then digitized by an ADC for further processing.

A current DAC circuit (IDAC) can be added to the front end of the receiver which has the same timing control with the LED driver to cancel the DC portion of the received current. The Idelta current is the difference between the Ipd and IDAC, which contains the AC portion of the received current and is only a small portion of the total current (<5%). The LED driver, IDAC and the ADC all use the same Vref voltage, in some embodiments, such that the low frequency noise of the Vref voltage will be canceled.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

Pulse-oximetry is a non-invasive method that may be used to monitor the saturation of a patient's hemoglobin. Pulse-oximetry typically utilizes a pair of small light-emitting diodes (LEDs) facing a photodiode through a translucent part of the patient's body, usually a fingertip or an earlobe. One LED is red, with wavelength of 660 nm, and the other is infrared, 905, 910, or 940 nm. Absorption at these wavelengths differs significantly between oxyhemoglobin and its deoxygenated form; therefore, the oxy/deoxyhemoglobin ratio can be calculated from the ratio of the absorption of the red and infrared light. The monitored signal bounces in time with the heart beat because the arterial blood vessels expand and contract with each heartbeat. By examining only the varying part of the absorption spectrum (essentially, subtracting minimum absorption from peak absorption), a monitor can ignore other tissues or nail polish, and discern only the absorption caused by arterial blood.

In measurements systems such as for pulse-oximetry, the desired signal has a very small amplitude that rides on a large ambient offset signal. In pulsed input measurement systems, such as for oximetry, the front end transimpedance amplifiers or gain amplifiers need to have a large bandwidth in order to support the pulsing input signals. The equivalent noise bandwidth of the front end is larger because of the large bandwidth for settling, even though the signal bandwidth of interest is much smaller The front end gain is usually restricted to avoid saturation of the front end due to the large offset signal in comparison to the signal of interest.

In practice, it is desirable to have a high front end gain without running the risk of saturation. This could be provided at a lower consumptive power while achieving a higher signal to noise ratio (SNR). There is developing interest to measure PPG signals continuously by incorporating PPG sensors/systems in devices that can be attached to a subject, for example, wrist band, watch, in-the-ear buds, etc. In such applications, these devices have to function with very low power and every photon emitted from the LED is precious as it is a drain on a battery. Furthermore, space constraints force the use of small photodiodes to collect diffuse light coming from the tissue. As a result, the signal is small and any reduction in noise of the system can be immediately applied to conserve battery power and increase the time to recharge or replace batteries.

Thus, much attention has been paid to reduce the noise of the receiver systems and noise in the LED drive circuits. Many noise reduction techniques for LED drivers and receivers require extra power. To make matters worse, many visible light LEDs themselves exhibit fairly large "1/f" noise in the generated light. This noise is a result of both 1/f noise in the LED driver as well as the physical mechanisms in the LED, such as the thermal fluctuations and the generation-recombination noise.

Since a heart beats at a relatively low frequency in the range of 0.5-5 Hz (30 to 300 beats per minute), this low frequency noise essentially limits the ability to measure the PPG signal. This becomes even more crucial for blooc oxygen saturation (SpO2) systems where accurate determinations of both AC and DC components of the PPG signal must be made.

Accordingly, the inventor perceives a need in the art for PPG system that permits reduction of noise in PPG signals captured by such systems.

FIG. 1 depicts an exemplary wearable vital sign monitor (VSM) 100 comprising plethysmograph (PPG) and electrocardiogram (ECG or EKG) measurements, in accordance with some embodiments of the disclosure provided herein. In one embodiment, a wearable PPG/ECG device 120 is disclosed. Wearable PPG/ECG device 120 is implemented based on subsequent discussion and embodiments, at least in part, using a single analog front end (AFE).

In practice, user 110 creates a biopotential using arm 130 opposite of arm 140 whereon the wearable PPG/ECG device 120 is disposed. Wearable PPG/ECG device 120 also induces PPG measuring device. This is disclosed in greater detail in application Ser. No. 14/500,129 entitled, "LOW FREQUENCY NOISE IMPROVEMENT IN PLETHYSMOGRAPHY MEASUREMENT SYSTEMS," which hereby incorporated by reference in its entirety.

In some embodiments, VSM is used to determine at least one of PPG (Photoplethysmography), ECG/EKG (Electrocardiogram), Bio-Z (Bio-Impedance), HRM (Heart Rate Monitor), HRV (Heart Rate Variability), SPO2 (Saturation level of Pulse Oxygen), BIA (Body impedance Analysis), Hydration analysis, CNIBP (Cuff-less Non-Invasive Blood Pressure) and PWV (Pulse Wave Velocity).

Pulse wave velocity (PWV) is the velocity at which the arterial pulse propagates through the circulatory system. PWV is used clinically as a measure of arterial stiffness. It is easy to measure invasively and non-invasively in humans, is highly reproducible, has a strong correlation with cardiovascular events and all-cause mortality and an indicator of target organ damage and a useful additional test in the investigation of hypertension. Additionally, high pulse wave velocity (PWV) has also been associated with poor lung function.

A heart rate monitor (HRM) is a personal monitoring device that allows one to measure/display heart rate in real time or record the heart rate for later study. It is largely used to gather heart rate data while performing various types of physical exercise. Measuring electrical heart information is referred to as Electrocardiography (ECG or EKG).

Medical heart rate monitoring used in hospitals is usually wired and usually multiple sensors are used. Portable medical units are referred to as a Holter monitor. Consumer heart rate monitors are designed for everyday use and do not use wires to connect.

Electrocardiography is the process of producing an electrocardiogram (ECG or EKG). It is a graph of voltage versus time of the electrical activity of the heart using electrodes placed on the skin. These electrodes detect the small electrical changes that are a consequence of cardiac muscle depolarization followed by repolarization during each cardiac cycle (heartbeat). Changes in the normal ECG pattern occur in numerous cardiac abnormalities, including cardiac rhythm disturbances (such as atrial fibrillation and ventricular tachycardia), inadequate coronary artery blood flow (such as myocardial ischemia and myocardial infarction), and electrolyte disturbances (such as hypokalemia and hyperkalemia).

Heart rate variability (HRV) is the physiological phenomenon of variation in the time interval between heartbeats. It is measured by the variation in the beat-to-beat interval. Other terms used include: "cycle length variability", "R-R variability" (where R is a point corresponding to the peak of the QRS complex of the ECG wave; and RR is the interval between successive Rs), and "heart period variability."

Methods used to detect beats include: ECG, blood pressure, ballistocardiograms, and the puke wave signal derived from a photoplethysmograph (PPG). ECG is considered superior because it provides a dear waveform, which makes it easier to exclude heartbeats not originating in the sinoatrial node. The term "NN" is used in place of RR to emphasize the fact that the processed beats are "normal" beats.

Hydration analysis comprises estimating the amount of water in a subject. In extreme cases of low hydration, oral rehydration therapy (ORT) may be applied. ORT is a type of fluid replacement used to prevent and treat dehydration due to activity, but especially due to diarrhea. It involves drinking water with modest amounts of sugar and salts, specifically sodium and potassium.

The current blood pressure (BP) measurement devices are mostly built on the principle of auscultation, oscillometry or tonometry, all of which use an inflatable cuff to occlude or unload the artery. The need of a cuff in these devices limits the further reduction in size and power consumption, and restricts the frequency and ease of their usage. In one or more embodiments, the present disclosure proposes a cuffless and noninvasive technique for measuring BP by pulse transit time.

Figure 2:
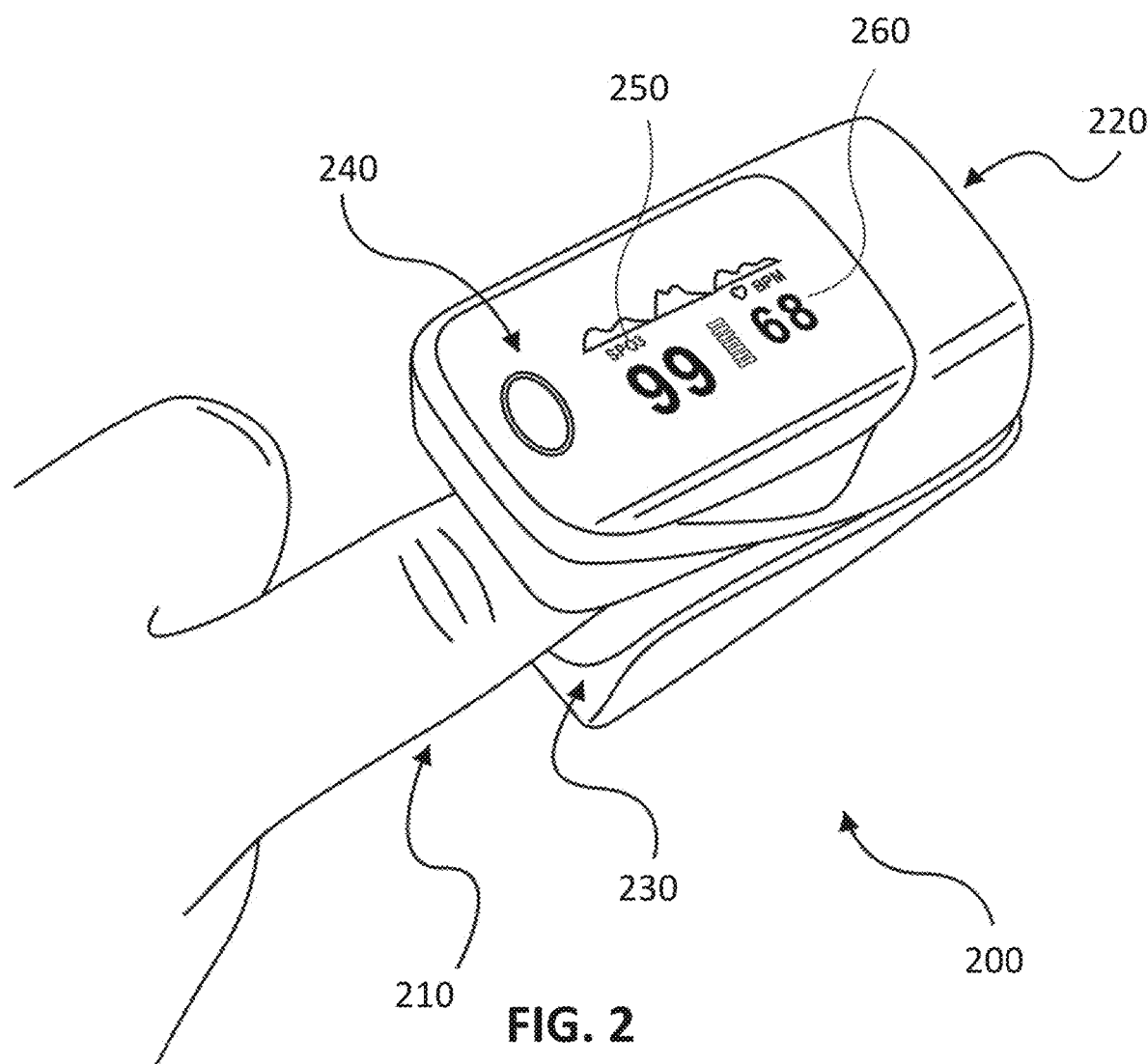
FIG. 2 shows an exemplary pulse oximeter device, in accordance with others embodiments of the disclosure provided herein.

FIG. 2 shows an exemplary puke oximeter device 200, in accordance with others embodiments of the disclosure provided herein. Pulse oximeter device 200 comprises body 220, function button 240, $SpO_2$ display 250, PR display 260, and finger orifice 230.

Body 220 is constructed in a spring-loaded clothespin fashion. It allows the orifice 230 to securely but safely damp onto a patient's finger 210. Depending on embodiment/model, function button 240 can be used for on-off power, cycling through modes, cycling through displays and/or checking battery power levels, any of which are not beyond the scope of the current disclosure.

$SpO_2$ display 250 outputs current blood oxygen saturation level as a percentage (unitless). Blood oxygen saturation level ($SpO_2$) is a measure of the amount of oxygen carried in the hemoglobin. $SpO_2$ is expressed as a percentage of the maximum amount of oxygen that hemoglobin in the blood can carry. Since hemoglobin accounts for over 90% of oxygen in blood, $SpO_2$ also measures the amount of oxygen in blood. PR display 260 outputs current pulse rate in units of beats per minute (bpm).

Figure 3:
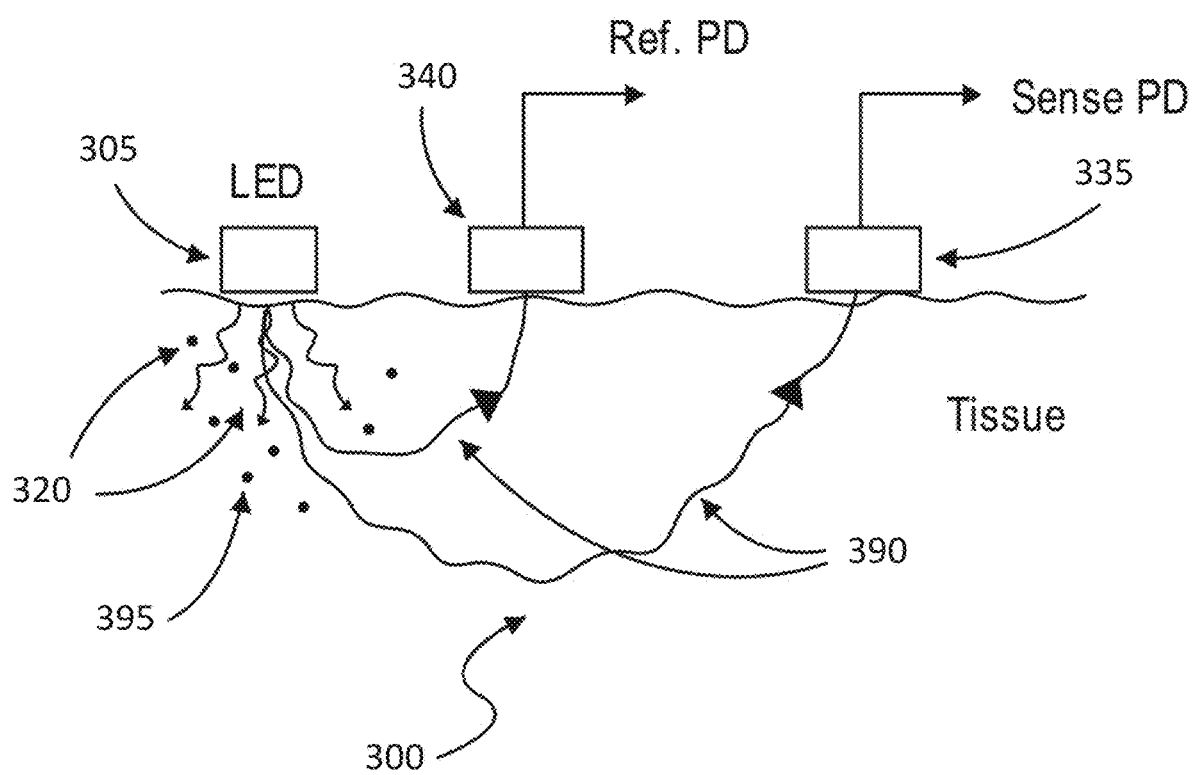
FIG. 3 illustrates an exemplary pulse oximeter in operation, in accordance with others embodiments of the disclosure provided herein.

FIG. 3 illustrates an exemplary pulse oximeter 300 in operation, in accordance with others embodiments of the disclosure provided herein. Exemplary pulse oximeter 300 comprises light emitting diode (LED) 305, sense detector 335, and reference detector 340. One skilled in the art will appreciate that some circuit elements have been omitted but that the principle remains the same as one or more of the previous embodiments.

In practice, light emitting diode (LED) 305 produces light 320 which in turn get scattered off of a predetermined chemical, e.g., $SpO_2$, within the tissue of a subject (patient). Subsequently scatter light 390 gets detected by either reference detector 340 or sense detector 335, depending on scattering trajectory and mean-free-path. This is a function of the light wavelength and chemical interaction which is known in the art.

In one or more embodiments, a separate photodiode may be deployed to act as reference channel to eliminate low frequency variations in the LED's output due to temperature and supply variations. Since a heart beats at roughly 1 Hz, this low-frequency elimination of LED's variation as well as any variation in gains allows one to reach high SNR even with noisy power supplies that generally add lots of noise and systematic variations at low frequencies.

In yet another embodiment associated with FIG. 3, two photodiodes can be used with one closer to the LED designated as the reference PD while the one further away acting as signal PD. In this case, even the variation in the LED's light coupling to the tissue becomes common mode and are eliminated. This will allow more precise measurement of the tissue scattering and absorption compounded with ambient light cancellation which will now be discussed in greater detail.

Figure 4:
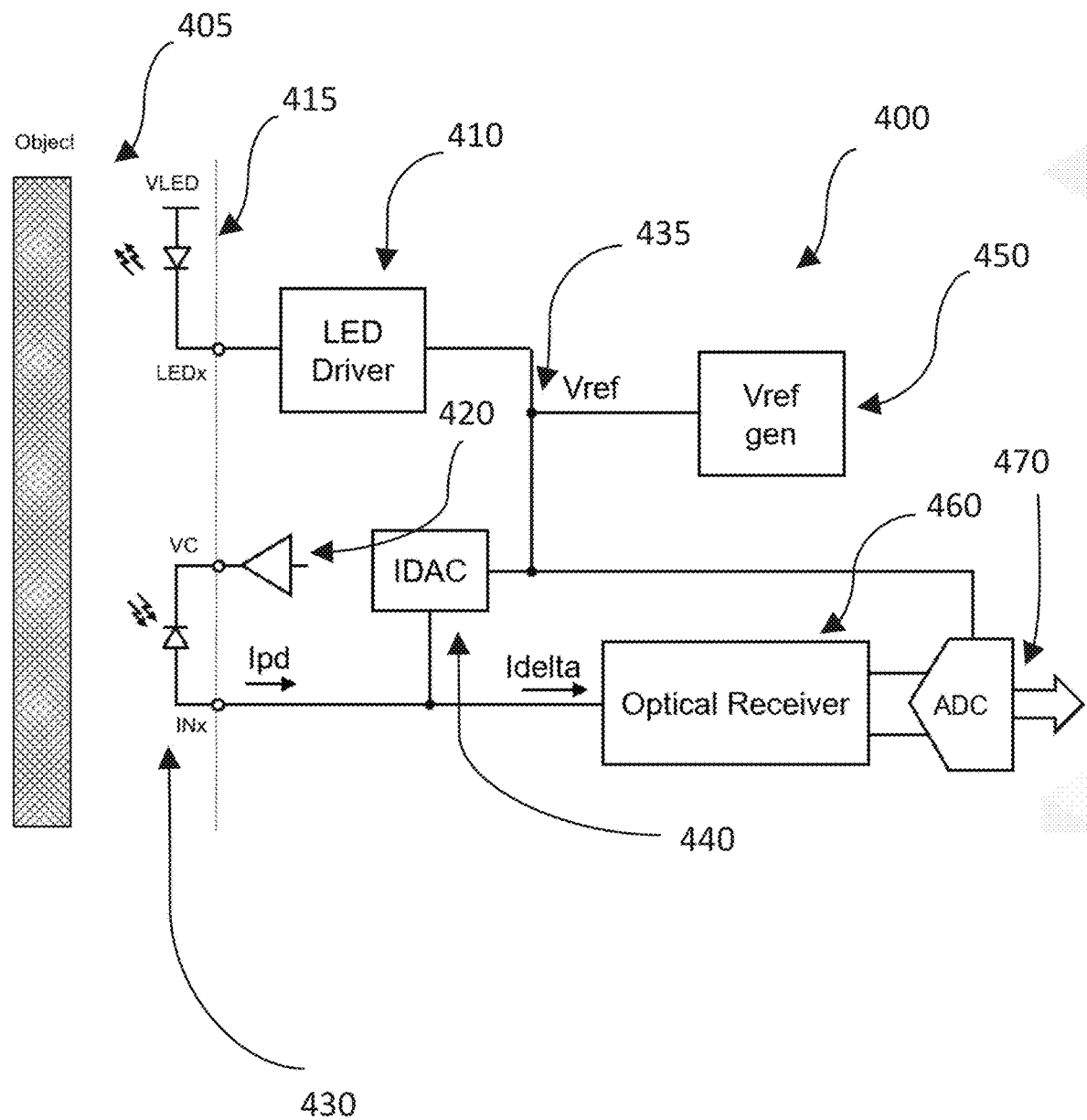
FIG. 4 depicts an exemplary schematic of an exemplary optical front end, in accordance with others embodiments of the disclosure provided herein.

FIG. 4 depicts an exemplary schematic of an exemplary optical front end 400, in accordance with others embodiments of the disclosure provided herein. Optical front end 400 comprises light emitting diode (LED) driver 410, VLED 415, photodetector 430, optical receiver 460, IDAC 440, Vref generator 450, analog to digital converter 470, and Vref node 435.

In one or more embodiments, the present disclosure provides a low noise cancellation, method and apparatus for optical front end. In practice, the optical front end 400 has a single-ended photo-diode 430 connected to optical receiver 460 which generates differential outputs to then drive ADC 470. The photo-diode 430 current will include the reflected light off an object 405 from the transmitter and the ambient light from the environment.

The pulsed light from object is dominated by the pulse itself. Specifically, object variations account for a small portion of the received signal. A current DAC (IDAC) 440 circuit is used to control gain to keep the optical receiver 460 within desirable bounds. In some embodiments, IDAC 440 is controlled by an AGC (automatic gain control) algorithm. The AGC can be used to decide an IDAC control code, which will toggle the IDAC code with some defined sequence and see if the residue current Idelta (Idelta=Ipd-IDAC) is small enough.

In several embodiments, Vref voltage 435 is shared LED driver 410, IDAC 440 and ADC 470. As one of ordinary skill in the art can appreciate, this gives rise to the noise cancellation, because the Vref noise often appears as the amplitude noise in the received photo-diode current. The timing of the pulse is decided by a timing circuit, which is usually a clocking circuit or an oscillator but can be any suitable device.

In one or more embodiments, the photo-diode (PD) 430 is reverse biased by amp 420 with its cathode connected to the VC node and with its anode connected to the optical receiver 460 input, such that the PD 430 current Ipd is always in one direction. As is known in the art, increasing the reverse bias producing greater sensor sensitivity, however at the risk of pushing the optical receiver 460 out of its linear region and possibly into saturation.

This is exacerbated due to the photo-diode 430 current Ipd including the reflected light from the transmitter (an LED 415) and the ambient light from the environment. In a dynamic environment, such as, found on a wearable device, the background ambient light is ever changing and can easily overwhelm the transmitter signal reflect off an object.

A current DAC circuit (IDAC) 440 is added at the front of the TIA 455 input to cancel the ambient light, such that the optical receiver 460 input current only contains the compensated light signal and maintain good signal quality. A DAC produces a quantized (discrete step) analog output in response to a binary digital input code. The digital input may be TTL, ECL, CMOS, or LVDS, while the analog output may be either a voltage or a current, as is reflected in the present embodiment.

To generate the output, a reference quantity (either a voltage or a current) is divided into binary and/or linear fractions. Then the digital input drives switches that combine an appropriate number of these fractions to produce the output. The number and size of the fractions reflect the number of possible digital input codes, which is a function of converter resolution or the number of bits (N) in the input code. For N bits, there are $2^N$ possible codes. The analog output of the DAC output is the digital fraction represented as the ratio of the digital input code divided by $2^N$ times the analog reference value.

In general, IDAC 440 receives a digital code and produces a current in opposite direction of Ipd. Specifically, IDAC 440 produces a current equal and opposite to that engendered the pulse produced by LED 415. One skilled in the art will appreciate the time which mitigates the causation of flicker noise. Specifically, node Vref 435, produce by Vref generator 450, is tied to LED driver 410, IDAC 440, and ADC 470. By synchronizing the synchronizing phase of pulse generate by Vref generator 450, Idelta current received by optical receiver 460 essential becomes a DC offset signal.

Figure 5:
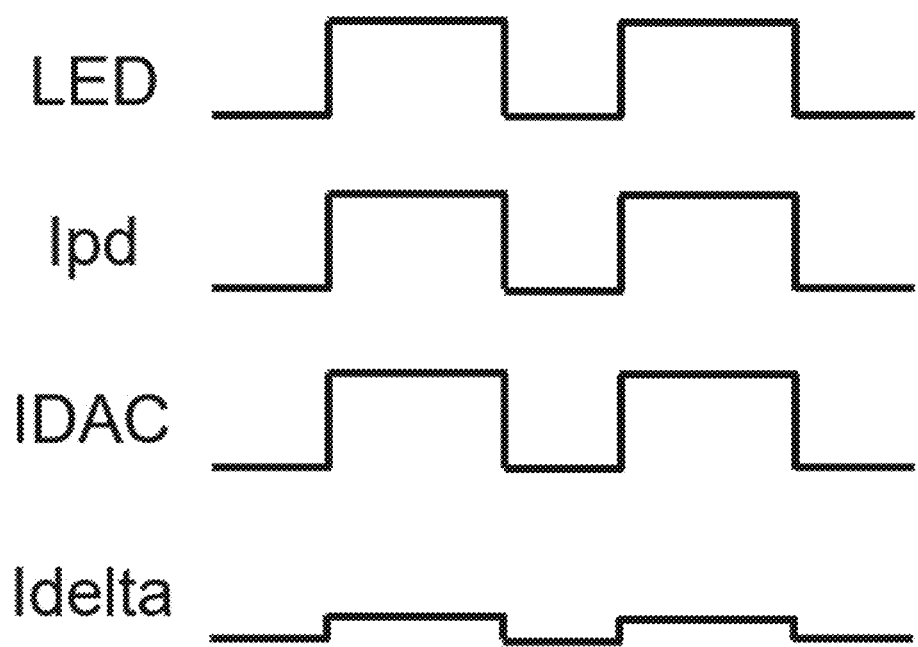
FIG. 5 demonstrates an exemplary timing diagram used to control feedback in an optical front end, in accordance with others embodiments of the disclosure provided herein.

FIG. 5 demonstrates an exemplary timing diagram used to control feedback in an optical front end, in accordance with others embodiments of the disclosure provided herein. The drawing shows the Optical Measurement system, which has a transmitter to drive an LED and a receiver connected to a photodiode.

The LED driver will generate a pulse signal to drive the LED and act as the radiation source for the optical measurement. The receiver will convert the received photodiode current to a voltage signal. And then it will be digitized by an ADC for further processing.

A current DAC circuit IDAC is added at the front of the receiver and has the same timing control with the LED driver to cancel the DC portion of the received current. The Idelta current is the difference between Ipd and IDAC, which contains the AC portion of the received current and is only a small portion of the total current (<5%).

Figure 6:
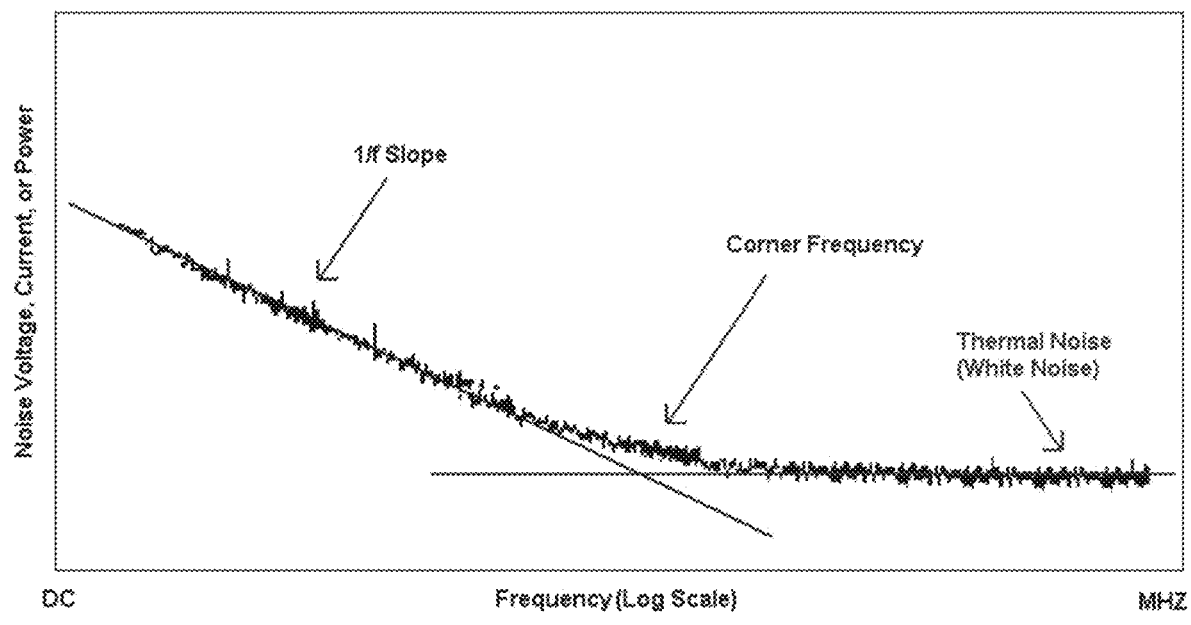
FIG. 6 is a graphical illustration of flicker noise as a function of frequency, in accordance with others embodiments of the disclosure provided herein.

FIG. 6 is a graphical illustration of flicker noise as a function of frequency, in accordance with others embodiments of the disclosure provided herein. Flicker noise is found in all active electronic components as well as some of the passive devices, and like shot noise, is associated with a DC current flow. A characteristic property of this noise is that its magnitude decreases with frequency, and therefore, is sometimes referred to as 1/f noise.

Flicker noise generally dominates at low frequencies for a properly designed system while the white noise sources become dominant at higher frequencies. Flicker noise corner frequency, fc is the frequency where the magnitudes of the white and flicker noises of a device are equal. The power spectrum density (PSD) of a system output is typically similar to the illustration in FIG. 6.

The power spectrum $S_{xx}$ of a time series describes the distribution of power into frequency components composing that signal. According to Fourier analysis, any physical signal can be decomposed into a number of discrete frequencies, or a spectrum of frequencies over a continuous range. The statistical average of a certain signal or sort of signal (including noise) as analyzed in terms of its frequency content, is called its spectrum.

When the energy of the signal is concentrates around a finite time interval, especially if its total energy is finite, one may compute the energy spectral density. More commonly used is the power spectral density (or simply power spectrum), which applies to signals existing over all time, or over a time period large enough (especially in relation to the duration of a measurement) that it could as well have been over an infinite time interval. The power spectral density (PSD) then refers to the spectral energy distribution that would be found per unit time, since the total energy of such a signal over all time would generally be infinite. Summation or integration of the spectral components yields the total power (for a physical process) or variance (in a statistical process), identical to what would be obtained by integrating $X^2(t)$ over the time domain, as dictated by Parseval's theorem.

The spectrum of a physical process X(t) often contains essential information about the nature of x. For instance, the pitch and timbre of light detection are immediately determined from a spectral analysis. The color of a light source is determined oy the spectrum of the electromagnetic wave's electric field as it fluctuates at an extremely high frequency. Obtaining a spectrum from time series such as these involves the Fourier transform, and generalizations based on Fourier analysis.

In mathematics, Parseval's theorem usually refers to the result that the Fourier transform is unitary; loosely, that the sum (or integral) of the square of a function is equal to the sum (or integral) of the square of its transform. It originates from a 1799 theorem about series by Marc-Antoine Parseval, which was later applied to the Fourier series. It is also known as Rayleigh's energy theorem, or Rayleigh's identity, after John William Strutt, Lord Rayleigh.

The LED driver circuit needs a reference voltage Vref, which comes from a Vref gen circuit. This Vref gen circuit is typically a bandgap circuit in modern CMOS process, which has low-frequency 1/f noise or flicker noise from the CMOS devices. The frequency band of interest of this low-frequency noise is as low as 1 mHz. The maximum frequency can be up to 10 kHz. This frequency is similar with a typical human heartbeat frequency, so it will interfere with the heart rate monitoring system using optical measurement system.

Figure 7:
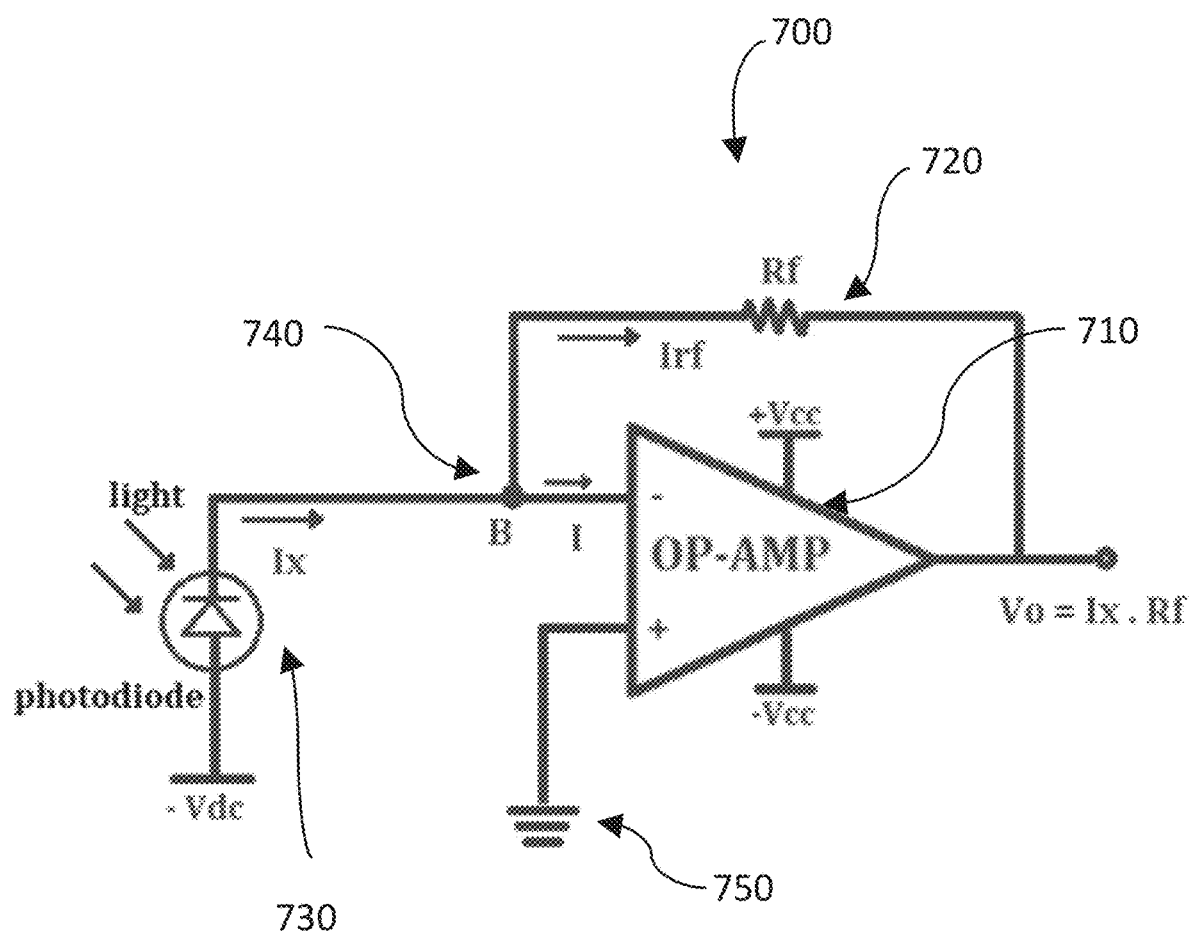
FIG. 7 shows an exemplary current to voltage converter, in accordance with others embodiments of the disclosure provided herein.

FIG. 7 shows an exemplary current to voltage converter 700, in accordance with others embodiments of the disclosure provided herein. current to voltage converter 700 comprises photodiode 730, node B 740, ground 750, feedback resister 720, op-amp 710.

In operation, photodiode 730 is reversed biased and produces a current when photons are incident on the semi-conductive active layer. The current produced by photodiode 730 passes through feedback resister 720 to create a potential over the negative input of op-amp 710 and its output thereof. Depending on how the devices are biased (e.g., -Vdc), node B may become a virtual/floating ground.

While simple embodiments use pulses are used in object detection. However, any suitable waveform is not beyond the scope of the present disclosure, such as, sine wave, square-wave, sawtooth, ramp, pulse train, triangle, etc. These waveforms can be either repetitive or single-shot such as provided by an internal or external trigger source like that provided by the FSM. In fact, no AC is necessary for calibration pursuant to the present disclosure.

However, one skilled in the art will recognize the utility of a pulse sequence repeated several times to perform sampling accumulation which yields better signal quality, because the noise will be averaged by sampling accumulation. However, the ambient will change over time, so it is better to sample the ambient just before each LED pulse and refresh the DAC control for each pulse sequence. In this way, the latency between the ambient sampling and ambient cancellation is small.

In some embodiments, one or more optical filters are chosen to match the light source. For example, if a midwave infrared (MWIR) LED is used as a light source, a dichroic filter centered between 3-5 μm could be placed over the photodetector. A dichroic filter, thin-film filter, or interference filter is a very accurate color filter uses to selectively pass light of a small range of colors while reflecting other colors. By comparison, dichroic mirrors and dichroic reflectors tend to be characterized by the color(s) of light that they reflect, rather than the color(s) they pass.

While dichroic filters are used in the present embodiment, other optical filters are not beyond the scope of the present invention, such as, interference, absorption, diffraction, grating, Fabry-Perot, etc. An interference filter consists of multiple thin layers of dielectric material having different refractive indices. There also may be metallic layers. In its broadest meaning, interference filters comprise also etalons that could be implemented as tunable interference filters. Interference filters are wavelength-selective by virtue of the interference effects that take place between the incident and reflected waves at the thin-film boundaries. In other embodiments, a color wheel with an optical chopper can be used as a filter.

In some embodiments a collimating lens can be used to help direct light from the light source to the object and/or focus incident light to the filter. In optics, a collimator may consist of a curved mirror or lens with some type of light source and/or an image at its focus. This can be used to replicate a target focused at infinity with little or no parallax. The purpose of the collimating lens is to direct the light rays in coaxial light path toward the photodetector.

In one or more embodiments, the light source is an infrared light emitting diode (LED), such as, Short Wavelength Infrared (SWIR), Medium Wavelength Infrared (MWIR), and Long Wavelength Infrared (LWIR). However, other embodiments can have light emitting diodes having shorter wavelengths, such as that in the visible or ultraviolet regime. In yet other embodiments, a plurality of multiple wavelengths can be used. Any suitable, compact light producing device is not beyond the scope of the present disclosure—whether, broadband lamps, coherent, incandescent, incoherent bulb, lasers, or even thermal black-body radiation, etc.

In some embodiments, photodetectors are used as transducers to sense the light, both background and produced. Photodetectors are sensors of light or other electromagnetic energy. Photodetectors have p-n junctions that converts light photons into current. The absorbed photons make electron-hole pairs in the depletion region, which is uses to detect received light intensity. In some embodiments, photodetector are photodiodes or phototransistors. However, any light detecting means, e.g., avalanche, photo-multiplier tube, etc. is riot beyond the scope of the present disclosure.

FIGS. 8-11 illustrate different applications for sensor systems of the foregoing embodiments.

Figure 8:
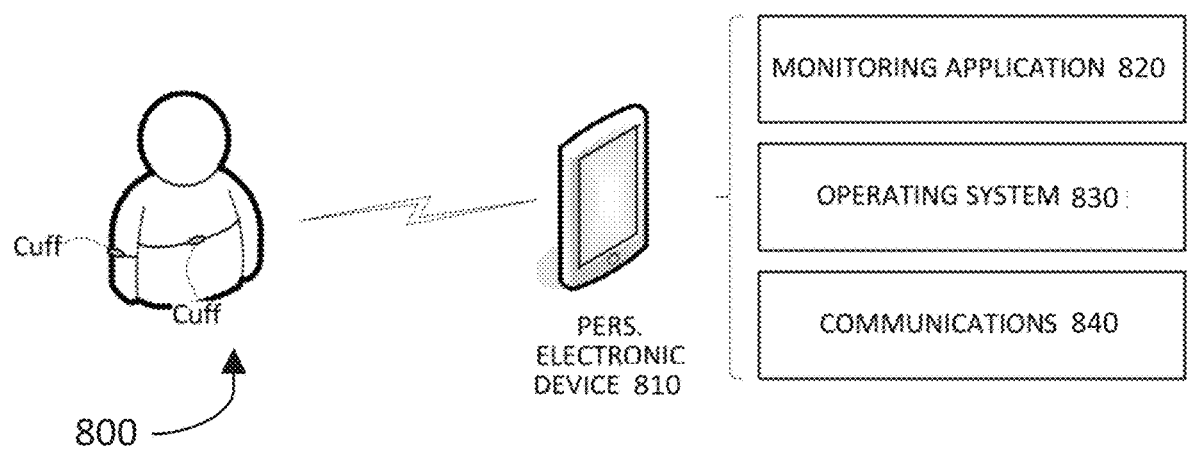
FIG. 8 depicts another exemplary wearable vital sign monitor (VSM), in accordance with some embodiments of the disclosure provided herein.

FIG. 8 depicts another exemplary wearable vital sign monitor (VSM), in accordance with some embodiments of the disclosure provides herein. In the embodiment illustrated in FIG. 8, for example, the sensor system with cancelation may be integrated into a cuff 800 that may be worn about some portion of a subject's body.

Cuffs are illustrated as provided about the arm or the chest of a subject. Alternative they may be integrated into headphones that place sensors in contact with the ears, into headbands that may place the sensors in contact with skin about the forehead, into wristbands, etc. The sensors may communicate with a personal electronic device 810 via wireless communications transceivers such as Bluetooth.

The personal electronic device 810 may include a monitoring application 820 to analyze signals reported to it by the sensors. The monitoring application 820 may interface with an operating system 830 and communication devices 840 within the electronic device 810 to perform its operations.

The personal electronic device 810 may be provided as a smartphone, tablet computer, personal heartrate monitor or other electronic device that collects physiological data regarding the subject. The PPG sensor systems discussed herein may be integrated with other fitness sensors that gather physiological data through other means.

Figure 9:
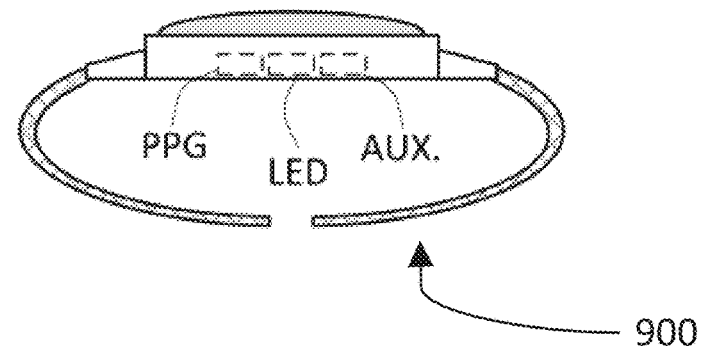
FIG. 9 depicts yet another exemplary wearable vital sign monitor (VSM), in accordance with some embodiments of the disclosure provided herein.

FIG. 9 depicts yet another exemplary wearable vital sign monitor (VSM), in accordance with some embodiments of the disclosure provided herein.

In the embodiment illustrated in FIG. 9, the sensor systems may be integrated into a wristwatch 900 or other personal accessory that is worn on a subject's body in contact with some portion of the subject's tissue. In addition to sensors, the accessory may include processors to perform analytics of the signals generated by the sensors and to derive PPG data. The wristwatch may have a display and associated controls that may display derived PPG data on command.

Figure 10:
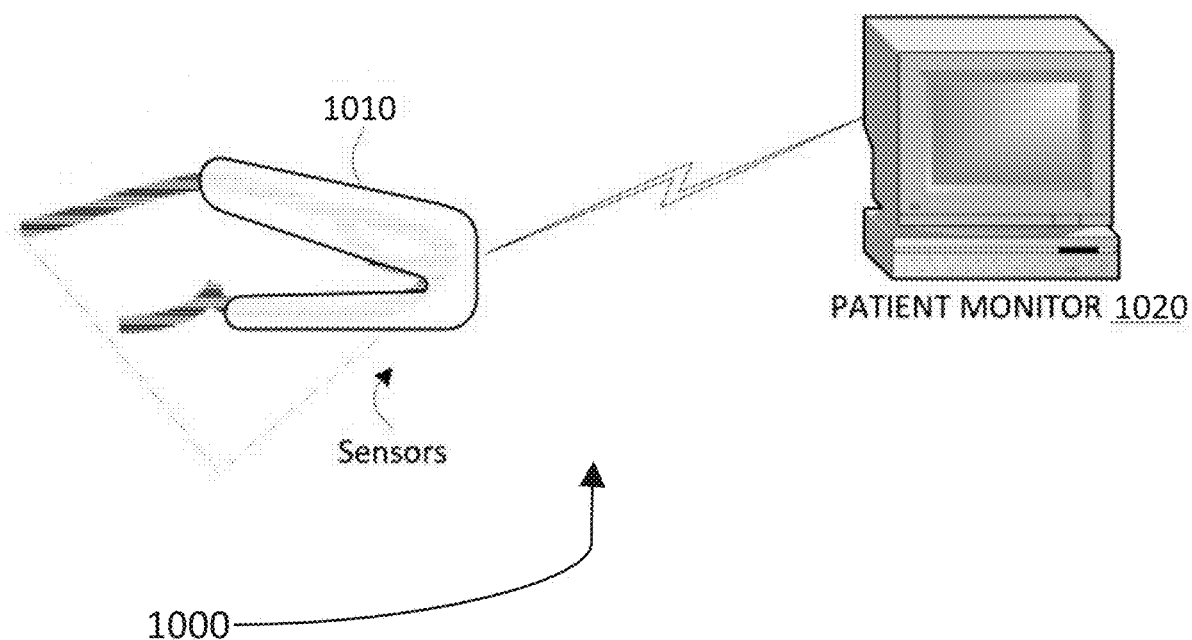
FIG. 10 depicts an exemplary finger cuff and vital sign monitoring (VSM) system, in accordance with some embodiments of the disclosure provided herein.

FIG. 10 depicts an exemplary finger cuff and vital sign monitoring (VSM) system, in accordance with some embodiments of the disclosure provided herein. FIG. 10 illustrates application of the sensor systems in a medical environment. In this embodiment, the sensors may be integrated into a sheath 1010 that is affixed to some portion of a patient's tissues (in this example, the patient's finger). The sensors may generate signals that are reported to monitoring equipment 1020 by wire-line or wireless communication link. The patient monitor 1020 may include analytics to derive physiological data from the signals reported to it by the sensors. The patient monitor 1020 also may support other types of sensors (not shown) and may generate other analytics therefrom.

Select Examples

Example 1 provides a method for canceling low frequency noise comprising producing a signal waveform, receiving the waveform at a driver, producing light in response to the received signal waveform, illuminating an object with the light, receiving the light at a photodetector, compensating for the produced signal waveform with a current to voltage compensator, receiving the compensated signal at an optical receiver having an input and output, and sampling the output of the optical receiver with an analog to digital converter (ADC).

Example 2 provides for a method for canceling low frequency noise according to any of the preceding and/or proceeding examples, wherein one or more of ADC, driver, and current to voltage compensator share a reference voltage.

Example 3 provides for a method for canceling low frequency noise according to any of the preceding and/or proceeding examples, wherein the reference voltage is controlled by a timing circuit or oscillator.

Example 4 provides for a method for canceling low frequency noise according to any of the preceding and/or proceeding examples, wherein the ADC, driver, and current to voltage compensator are timed to the same produced waveform.

Example 5 provides for a method for canceling low frequency noise according to any of the preceding and/or proceeding examples, wherein the current to voltage compensator is an IDAC.

Example 6 provides for a method for canceling low frequency noise according to any of the preceding and/or proceeding examples, wherein the optical receiver is an op-amp.

Example 7 provides for a method for canceling low frequency noise according to any of the preceding and/or proceeding examples, wherein the light is produced by a light emitting diode (LED).

Example 8 provides for a method for canceling low frequency noise according to any of the preceding and/or proceeding examples, wherein the photodetector is a photodiode.

Example 9 provides for a method for canceling low frequency noise according to any of the preceding and/or proceeding examples, wherein the compensation includes subtracting the reference signal from the received photodetector signal.

Example 10 provides for a method for canceling low frequency noise according to any of the preceding and/or proceeding examples, wherein the signal waveform is a pulse train.

Example 11 provides for an apparatus for canceling low frequency noise comprising a driver configures to power a light source, a reference voltage generator for producing a voltage, Vref. a current source, a receiver in electrical communication with the current source, and an analog to digital converter (ADC) configured to sample the output of the receiver, wherein at least two of driver, current source, and ADC share Vref.

Example 12 provides for an apparatus for canceling low frequency noise according to any of the preceding and/or proceeding examples further comprising a light sensor, the light sensor in electrical communication with the receiver and current source.

Example 13 provides for an apparatus for canceling low frequency noise according to any of the preceding and/or proceeding examples further comprising a timing module, the timing module is in electrical communication with the reference voltage generator.

Example 14 provides for an apparatus for canceling low frequency noise according to any of the preceding and/or proceeding examples, wherein the timing module is a clock circuit.

Example 15 provides for an apparatus for canceling low frequency noise according to any of the preceding and/or proceeding examples, wherein the timing module comprises an oscillator.

Example 16 provides for an apparatus for canceling low frequency noise according to any of the preceding and/or proceeding examples, wherein the driver, current source, and ADC share Vref.

Example 17 provides for an apparatus for canceling low frequency noise according to any of the preceding and/or proceeding examples, wherein Vref is controlled by the timing module, at least in part.

Example 18 provides for an apparatus for canceling low frequency noise according to any of the preceding and/or proceeding examples, wherein Vref is a pulse train.

Example 19 provides for an apparatus for canceling low frequency noise according to any of the preceding and/or proceeding examples, wherein the current source is an IDAC and configured to maintain a current range received by the receiver.

Example 20 provides for an apparatus for canceling low frequency noise comprising means for producing a signal waveform, means for receiving the waveform at a driver, means for producing light in response to the received signal waveform, means for illuminating an object with the light, means for receiving the light at a photodetector, means for compensating for the produced signal waveform with a current to voltage compensator, means for receiving the compensated signal at an optical receiver having an input and output, and means for sampling the output of the optical receiver with an analog to digital converter (ADC).

Numerous specific details have been set forth herein to provide a thorough understanding of the embodiments. It will be understood by those skilled in the art, however, that the embodiments may be practiced without these specific details. In other instances, well-known operations, components and circuits have not been described in detail so as not to obscure the embodiments. It can be appreciates that the specific structural and functional details disclosed herein may be representative and do not necessarily limit the scope of the embodiments.

The above description of illustrated embodiments, including what is described in the Abstract, is riot intended to be exhaustive or limiting as to the precise forms disclosed. While specific implementations of, and examples for, various embodiments or concepts are described herein for illustrative purposes, various equivalent modifications may be possible, as those skilled in the relevant art will recognize. These modifications may be made in light of the above detailed description, the Abstract, the Figures, or the claims.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present (disclosure, and that they may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data.

In some cases, the teachings of the present (disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least part y in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software.

In some embodiments, one or more of these features may be implementer in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface, Examples of output devices that may be used to provide a user interface include printers or display screens for visual presentation of output and speakers or other sound generating devices for audible presentation of output. Examples of input devices that may be used for a user interface induce keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules induce routines, programs, objects, components, data structures, etc. that performs particular tasks or implement particular abstract data types. Typically, the functionality of the program modules may be combined or distributed as desired in various embodiments.

The terms program or "software" are uses herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter or the source code may be converted (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Interpretation of Terms

All definitions, as defined and used herein, should be understood to control over dictionary definitions, definitions in documents incorporated by reference, and/or ordinary meanings of the defined terms. Unless the context clearly requires otherwise, throughout the description and the claims:

"comprise," "comprising," and the like are to be construed in an inclusive sense, as opposed to an exclusive or exhaustive sense; that is to say, in the sense of "including, out not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at east one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalent "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as we as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be dosed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method for canceling low frequency noise comprising:
   producing a signal waveform from a reference voltage generator;
   receiving the signal waveform at a driver;
   producing light in response to the received signal waveform;
   illuminating an object with the light;
   receiving the light at a photodetector;
   compensating for the produced signal waveform with a current to voltage compensator;
   receiving the compensated signal at an optical receiver having an input and output; and
   sampling the output of the optical receiver with an analog to digital converter (ADC);
   wherein driver and current to voltage compensator share the signal waveform from the reference voltage generator.

2. The method according to claim 1, wherein the ADC shares the signal waveform from the reference voltage generator.

3. The method according to claim 2, wherein the reference voltage generator is controlled by a timing circuit or oscillator.

4. The method according to claim 3, wherein the ADC, driver, and current to voltage compensator are timed to the same produced waveform.

5. The method according to claim 1 wherein the current to voltage compensator is an IDAC.

6. The method according to claim 2 wherein the optical receiver is an op-amp.

7. The method according to claim 1 wherein the light is produced by a light emitting diode (LED).

8. The method according to claim 1 wherein the photodetector is a photodiode.

9. The method according to claim 6 wherein the compensation includes subtracting the signal waveform from the received photodetector signal.

10. The method according to claim 1 wherein the signal waveform is a pulse train.

11. An apparatus for canceling low frequency noise comprising:
    a driver configured to power a light source;
    a reference voltage generator for producing an AC voltage, Vref;
    a current digital to analog converter;
    a receiver in electrical communication with the current digital to analog converter; and
    an analog to digital converter (ADC) configured to sample the output of the receiver;
    wherein the driver and current digital to analog converter share Vref.

12. The apparatus of claim 11 further comprising a light sensor, the light sensor in electrical communication with the receiver and current digital to analog converter.

13. The apparatus of claim 11 further comprising a timing module, the timing module is in electrical communication with the reference voltage generator.

14. The apparatus of claim 13, wherein the timing module is a clock circuit.

15. The apparatus of claim 13, wherein the timing module comprises an oscillator.

16. The apparatus of claim 13, wherein the driver, current source, and ADC share Vref.

17. The apparatus of claim 16, wherein Vref is controlled by the timing module, at least in part.

18. The apparatus of claim 17, wherein Vref is a pulse train.

19. The apparatus of claim 11, wherein the current digital to analog converter is configured to maintain a current range received by the receiver.

20. An apparatus for canceling low frequency noise comprising:
    means for producing a signal waveform from a reference voltage generator;
    means for receiving the signal waveform at a driver;
    means for producing light in response to the received signal waveform;
    means for illuminating an object with the light;
    means for receiving the light at a photodetector;
    means for compensating for the produced signal waveform with a current to voltage compensator;
    means for receiving the compensated signal at an optical receiver having an input and output; and
    means for sampling the output of the optical receiver with an analog to digital converter (ADC);
    wherein driver and current to voltage compensator share the signal waveform from the reference voltage generator.

* * * * *